United States Patent
Grewal et al.

(12)

(10) Patent No.: US 6,323,194 B1
(45) Date of Patent: Nov. 27, 2001

(54) MUSCARINIC AGONISTS AND ANTAGONISTS

(75) Inventors: Gurmit Grewal, Natick; Anna Toy-Palmer, Arlington; Xiong Cai, Belmont; George Mark Latham, Cambridge, all of MA (US)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 09/690,494

(22) Filed: Oct. 17, 2000

Related U.S. Application Data

(62) Division of application No. 09/567,785, filed on May 9, 2000, which is a division of application No. 09/375,149, filed on Aug. 16, 1999, now Pat. No. 6,093,724.
(60) Provisional application No. 60/096,977, filed on Aug. 18, 1998.

(51) Int. Cl.$^7$ .......................... A61K 31/439; A61P 25/04; C07D 487/18
(52) U.S. Cl. .................... 514/214.03; 514/183; 540/477; 540/581
(58) Field of Search .................................. 540/477, 581; 514/214.03, 183, 216.07

(56) References Cited

U.S. PATENT DOCUMENTS

| | | | |
|---|---|---|---|
| 4,739,074 | 4/1988 | Georgiev et al. | 548/411 |
| 5,578,602 | 11/1996 | Sauerberg et al. | 514/299 |
| 5,641,791 | 6/1997 | Sauerberg et al. | 514/339 |
| 5,952,339 | 9/1999 | Bencherif et al. | 514/294 |
| 5,955,470 | 9/1999 | Gittos | 514/294 |
| 5,986,100 | 11/1999 | Crooks et al. | 546/101 |
| 6,057,446 | 5/2000 | Crooks et al. | 546/97 |

FOREIGN PATENT DOCUMENTS

| | | |
|---|---|---|
| 0 316 718 | 5/1989 | (EP) . |
| WO 92/11261 | 7/1992 | (WO) . |
| WO 97/16451 | 5/1997 | (WO) . |
| WO 97/36906 | 10/1997 | (WO) . |
| WO 99/51601 | 10/1999 | (WO) . |

OTHER PUBLICATIONS

Eglen et al., "Selective Muscarinic Receptor Agonists and Antagonists," Pharmacology & Toxicology, vol. 78, 59–68 (1996).
Naguib et al., "Characterization of Muscarinic Receptor Subtypes That Mediate Atinociception in the Rat Spinal Cord," Anesth. Analg. 85:847–53 (1997).
Nemes et al., "Synthesis and Stereochemistry of 7,9–Distributed 3–Azabicyclo[3.3.1]nonanes," Liebigs Anal. Chem. (1993) (2), 179–182.
Bok et al., "Synthesis and Conformational Analysis of Exo– and Endo–7–Substituted–3–Azabicyclo[3.3.1]nonanes," Tetrahedron (1979), 35(2), 267–282.
Risch et al., "Synthesis and Deoxygenation of substituted 1–azaadamantane–4,6–diones," Chem. Ber. 125:459–465(1992).
Sauerberg et al., "Muscarinic Agonists as Analgesics. Antinociceptive Activity Versus $M_1$ Activity: SAR of Alkylthio–TZTP's and Related 1,2,5–Thiadiazole Analogs.", Life Sciences, vol. 56, No. 11/12, 807–814, 1995.

*Primary Examiner*—Mukund J. Shah
*Assistant Examiner*—Venkataraman Balasubramanian
(74) *Attorney, Agent, or Firm*—McDonnell Boehnen Hulbert & Berghoff

(57) ABSTRACT

The present invention provides novel compounds and pharmaceutical compositions thereof useful in the treatment of pain. The compounds of the present invention are azaadamantanes, azanoradamantanes and azahomoadamantanes.

8 Claims, No Drawings

MUSCARINIC AGONISTS AND ANTAGONISTS

This application is a division of U.S. patent application Ser. No. 09/567,785, filed May 9, 2000, which is a division of U.S. patent application Ser. No. 09/375,149, filed Aug. 16, 1999, U.S. Pat. No. 6,093,724, which claims the benefit of U.S. Provisional Application No. 60/096,977, filed Aug. 18, 1998.

BACKGROUND OF THE INVENTION

1. Field of the Invention

This invention relates to cholinergic receptor agonists and antagonists and their use as antinociception (pain relief) agents and as agents for the treatment of a variety of neurologic and psychiatric disorders. In particular, the invention relates to novel classes of azaadamantanes and azanoradamantanes.

2. Summary of the Related Art

The compounds of the invention have uses as cholinergic agonists and antagonists. As such they will have utility in modifying states where there is an imbalance in cholinergic function. An example of cholinergic deficiency is in Alzheimer's disease where there is degeneration of cholinergic neurons within the CNS. The postsynaptic muscarinic receptors in the forebrain and hippocampus persist and, therefore, muscarinic agonists have utility in treating AD by halting its progression and improving cognitive function. Cholinergic agonists also have utility in the treatment of other CNS disorders including schizophrenia or schizophreniform conditions, mania, bipolar disorders, depression and anxiety. Cholinergic agonists are particularly useful as analgesic agents and, therefore, have utility in the treatment of severe and chronic pain. Cholinergic agonists also have utility in alleviation of intraocular pressure such as found in glaucoma.

Many peripheral disease states have a basis in exaggerated cholinergic drive. Cholinergic antagonists therefore have utility in these conditions. Examples where muscarinic antagonists have utility are in bladder dysfunction, gastrointestinal motility disorders and obstructive airway disease such as COPD and asthma.

In particular, there has been considerable effort in the scientific/medical community to develop non-opiate painkillers which maintain the efficacy of opiates against severe and chronic pain but are devoid of the opiate liabilities of respiratory depression, constipation and dependence. The studies undertaken by various authors and researchers have demonstrated the importance of highly selective muscarinic agonists for use in antinociception (the treatment of pain) without the attendant undesirable side effects. The advantage of having a selective muscarinic agonist for blocking pain has been described in numerous publications. See for example, Sauerburg et al, *Life Sci.* 56, 807–814 (1995); Naguib et al., *Anesth. Analg.* 85, 847–85 (1997); Eglen & Watson, *Pharmacol. Toxicol.* 78, 59–68 (1996).

Jeppesen et al. WO 97/36906, entitled "Heterocyclic Compounds and their Preparation and Use," discloses compounds comprising an unsubstituted azatricyclic heptane attached directly to a substituted or unsubstituted aromatic heterocyclic group which is a 1,2,5-thiadiazole. The compounds are claimed to be useful in treating central nervous system ("CNS") diseases caused by malfunctioning of the muscarinic cholinergic system.

Macleod et al. WO 92/11261, entitled "4-Azatricyclo[2.2.1.0$^{2,6}$]heptanes and Pharmaceutical Compositions," discloses compounds comprising an unsubstituted azatricyclic heptane attached directly to a substituted or unsubstituted 5-membered aromatic heterocyclic group comprising two or three heteroatoms, at least one of which is nitrogen and another of which is oxygen or sulfur. Preferred aromatic heterocyclic groups include a 1,2,4-thiadiazole and a 1,3,4-thiadiazole. The compounds are claimed to be useful in treating neurological and mental illnesses whose clinical manifestations are due to cholinergic deficiency.

Sauerberg et al. U.S. Pat. No. 5,578,602, entitled "Certain 1-Azabicyclo[3.3.1]nonene Derivatives and Their Pharmacological Uses," discloses compounds comprising a substituted or unsubstituted azabicyclic ring comprising from between four to ten total atoms attached directly to a substituted or unsubstituted 5-membered aromatic heterocyclic group which is a 1,2,5-thiadiazole or a 1,2,5-oxadiazole. Preferred embodiments illustrate azabicyclic rings comprising 1-azabicyclo[3.3.1]nonene, 1-azabieyclo[3.2.3]octane, 1-azabicyclo[2.2.2]octane, or 1-aza-bicyclo[2.2.1]heptane. The compounds are claimed to be useful as muscarinic agonists.

Sauerberg et al. U.S. Pat. No. 5,641,791, entitled "Heterocyclic Compounds and Their Preparation and Use," discloses compounds comprising a substituted or unsubstituted azabicyclic octane attached directly to a substituted or unsubstituted 5-membered aromatic heterocyclic group which is a 1,2,5-thiadiazole or a 1,2,5-oxadiazole. The azabicyclic ring is 1-azabicyclo[2.2.2]octane. The compounds are claimed to be useful as muscarinic agonists.

Georgiev et al. U.S. Pat. No. 4,739,074, entitled "Adamantane Spiro-Pyrrolidene Derivatives," discloses compounds comprising an unsubstituted tricyclic decane attached directly to a substituted or unsubstituted 5-membered non-aromatic heterocyclic group comprising one heteroatom which is nitrogen. The compounds arc claimed to exhibit anti-Parkinson's activity.

Olesen et al., entitled, "3-(3-alkylthio-1,2,5-thiadiazol-4-yl)-1-azabicycles. Structure-activity relationships for antinociception mediated by central muscarinic receptors," discloses, as the title indicates, compounds of the structure:

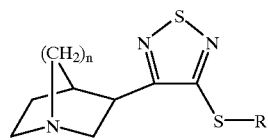

wherein n is 1 (azanorbornanylthiadizoles) or 2 (quinuclidinylthiadiazoles) and R is alkyl, that show high affinity for muscarinic receptors and induce antinociception in vivo.

Shannon et al., entitled "In Vivo Pharmacology of Butylthio[2.2.2] (LY297802/NNCC11-1053), An Orally Acting Antinociceptive Muscarinic Agonist" discloses (+)-3(S)-3-[4-butylthio-1,2,5-thiadiazol-3-yl]-1-azabicyclo[2.2.2]octane. This compound was selected for further study based on the results presented in the Olesen et al., supra. Shannon et al. suggests that this azabicyclo compound may be a selective M4 receptor agonist.

Despite the work done to date in the field there remains a need for antinociceptive agents.

SUMMARY OF THE INVENTION

The present invention brings a solution in the form of novel products that are useful as cholinergic receptor agonists and antagonists. In a preferred embodiment, the compounds of the invention can act selectively on certain muscarinic receptors, particularly on M4 receptors, with reduced cholinergic side effects. Consequently, they are well-suited for therapeutic use in the treatment of pain and other neurologic and psychiatric disorders. The compounds of the invention are members of novel classes of azaadamantanes, azanoradamantanes and azahomoadamantanes.

In addition, the invention provides pharmaceutical compositions comprising the compounds of the invention and methods of treating pain and neurologic and psychiatric disorders with the pharmaceutical compositions.

All patent applications, patents, and other publications recited herein are hereby incorporated by reference in their entirety.

DETAILED DESCRIPTION OF THE PREFERRED EMBODIMENTS

The Compounds

The novel compounds of the invention are azacyclic ring systems having the formula I

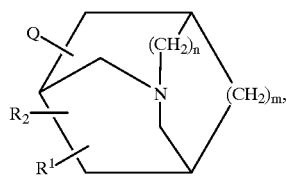

I including geometrical isomers, enantiomers, diastereomers, racemates, acid addition salts, salts thereof with a pharmaceutically acceptable acid, and prodrugs thereof, wherein
Q is

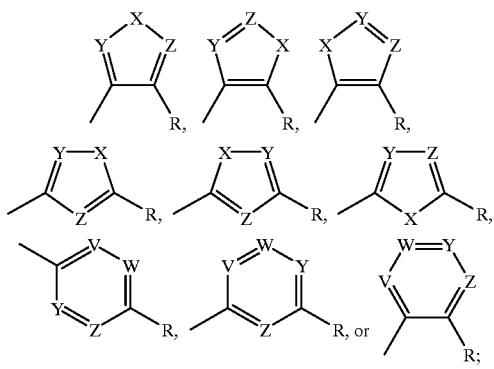

X is $CH_2$, NH, O or S;
V, W, Y and Z independently are CH or N;
n and m independently are 0, 1, 2, 3 or 4;
$R^1$ and $R^2$ are at any position on the azacyclic ring, including the point of attachment of the heterocycle Q, and independently are hydrogen, —OH, halogen, —$NH_2$, carboxy, straight or branched $C_{1-10}$-alkyl, $C_{1-10}$-alkenyl, or $C_{1-10}$-alkynyl, straight or branched $C_{1-10}$-alkoxy, or straight or branched $C_{1-10}$-alkyl substituted with —OH, —CN, —CHO, —OH, —$OR^3$, —$SR^3$, —$NH_2$, —$NHR^3$, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CH=$NOR^3$; or $R^1$ and $R^2$ independently are phenyl, phenoxy, benzoyl, benzyl or benzyloxycarbonyl, each of which is unsubstituted or substituted with halogen, —CN, $C_{1-10}$-alkyl, $C_{1-10}$-alkoxy, or $C_{1-10}$-alkylthio;
R is hydrogen, halogen, —CN, —CHO, —OH, —$OR^3$, —$SR^3$, —$NH_2$, —$NHR^3$, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CH=$NOR^3$; or
R is phenyl, phenoxy, benzoyl, benzyl or benzyloxycarbonyl, each is which is unsubstituted or substituted with halogen, —CN, $C_{1-15}$-alkyl, $C_{1-10}$-alkoxy, or $C_{1-10}$-alkylthio; or
R is a 5 or 6 membered saturated, partly saturated or aromatic heterocyclic ring containing one to three heteroatoms; and
$R^3$ and $R^4$ independently are straight, branched, or cyclic $C_{1-15}$-alkyl, $C_{2-15}$-alkenyl, $C_{2-15}$-alkynyl, or combinations thereof, or $R^3$ and $R^4$ independently are phenyl, phenoxy, benzoyl, benzyl or benzyloxycarbonyl groups, each of the foregoing of which are unsubstituted or substituted with H, halogen, —CN, $C_{1-15}$-alkyl, $C_{1-10}$-alkoxy, $C_{1-10}$-alkylthio, or aryl; or
$R^3$ and $R^4$ independently are 5 or 6 membered saturated, partly saturated or aromatic heterocyclic rings containing one to three heteroatoms.

In a preferred embodiment both m and n are 1 in structural formula I and the compounds of the invention have the structural formula:

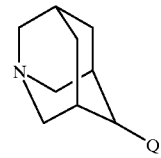

II wherein
Q is:

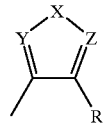

X is S,
Y and Z are N, and
R is $OR^3$ or $SR^3$.

In a particularly, preferred embodiment of the compounds of structural formula II, $R^3$ is —$CH_3$, —$CH_2CH_3$, —$CH_2CH_2CH_3$, —$CH_2CH_2CH_2CH_3$ or —$CH_2CH(CH_3)_2$.

The compounds of the present invention (i.e., Formulas I and II) are particularly useful to induce analgesia by selective agonism of the muscarinic M4 receptor. They are useful both in vivo (e.g., for the treatment of pain in mammals, preferably humans, in need thereof) as well as in vitro (e.g., to study the role of muscarinic M4 receptors in biological processes).

Definitions

Except as otherwise expressly indicated, the following definitions are employed herein:

The term alkyl refers to a saturated straight, branched, or cyclic (or a combination thereof) $C_1$–$C_{10}$ hydrocarbon and specifically includes, but is not limited to, methyl, ethyl, propyl, isopropyl, cyclopropylmethyl, cyclobutylmethyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term lower alkyl, as used herein, refers to a $C_1$ to $C_6$ saturated straight, branched, or cyclic (in the case of $C_6$) hydrocarbon, and specifically includes, but is not limited to, methyl, ethyl, propyl, isopropyl, butyl, isobutyl, t-butyl, cyclopropylmethyl, pentyl, cyclopentyl, cyclobutylmethyl, isopentyl, neopentyl, hexyl, isohexyl, cyclohexyl, 3-methylpentyl, 2,2-dimethylbutyl, and 2,3-dimethylbutyl.

The term alkylamino refers to an amino group that has an alkyl substituent.

The term alkynyl refers to a $C_2$ to $C_{10}$ straight or branched hydrocarbon with at least one triple bond.

The term lower alkynyl refers to a $C_2$ to $C_6$ alkynyl group, specifically including, but is not limited to, acetylenyl and propynyl.

The term aryl refers to phenyl, substituted phenyl, or heteroaryl (as further defined below) wherein the substituent is halo, alkyl, alkoxy, alkylthio, haloalkyl, hydroxyalkyl, alkoxyalkyl, methylenedioxy, cyano, C(O)(lower alkyl), carboxy, $CO_2$alkyl, amide, amino, alkylaamino and dialkylamino, and wherein the aryl group can have up to 3 substituents.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined for aryl groups.

A heteroatom is N, S, or O.

The term heterocyclyl, heterocyclic, heterocycle and variations thereof mean a cycloalkyl moiety substituted in the ring by one or more heteroatoms. Examples of heterocycles include, but are not limited to, pyrrolidinyl, piperidinyl, and piperazinyl.

The terms heteroaryl and heteroaromatic, as used herein, refer to an aromatic moiety that includes at least one heteroatom in the aromatic ring. Examples include, but are not limited to, furyl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term organic or inorganic anion refers to an organic or inorganic moiety that carries a negative charge and can be used as the negative portion of a salt.

The term "pharmaceutically acceptable application" refers to an organic or inorganic moiety that carries a positive charge and that can be administered in association with a pharmaceutical agent, for example, as a counterion in a salt.

The term "enantiomerically enriched composition or compound" refers to a composition or compound that includes at least 95% by weight of a single enantiomer of the compound.

The term pharmaceutically active derivative refers to any compound that upon administration to the recipient, is capable of providing directly or indirectly, the compounds disclosed herein.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Synthetic Schemes

The following synthetic schemes illustrate how compounds according to the invention can be made. Those skilled in the art will be able to routinely modify and/or adapt the following schemes to synthesize any compound of the invention.

Synthesis of 1-Azaadamantane-4-one Starting Material

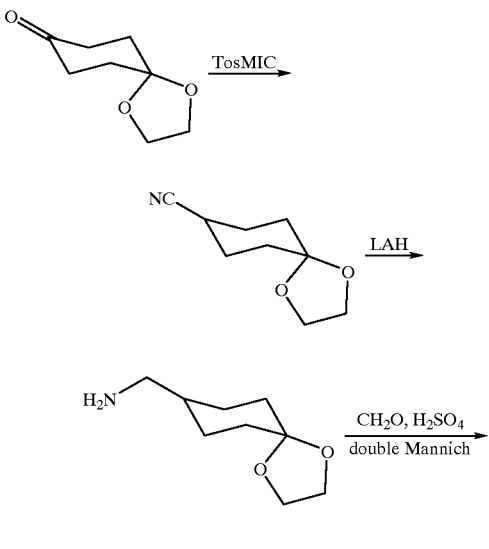

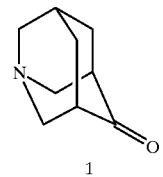

1

Synthesis of Azaadamantanes from 1-Azaadamantane-4-one
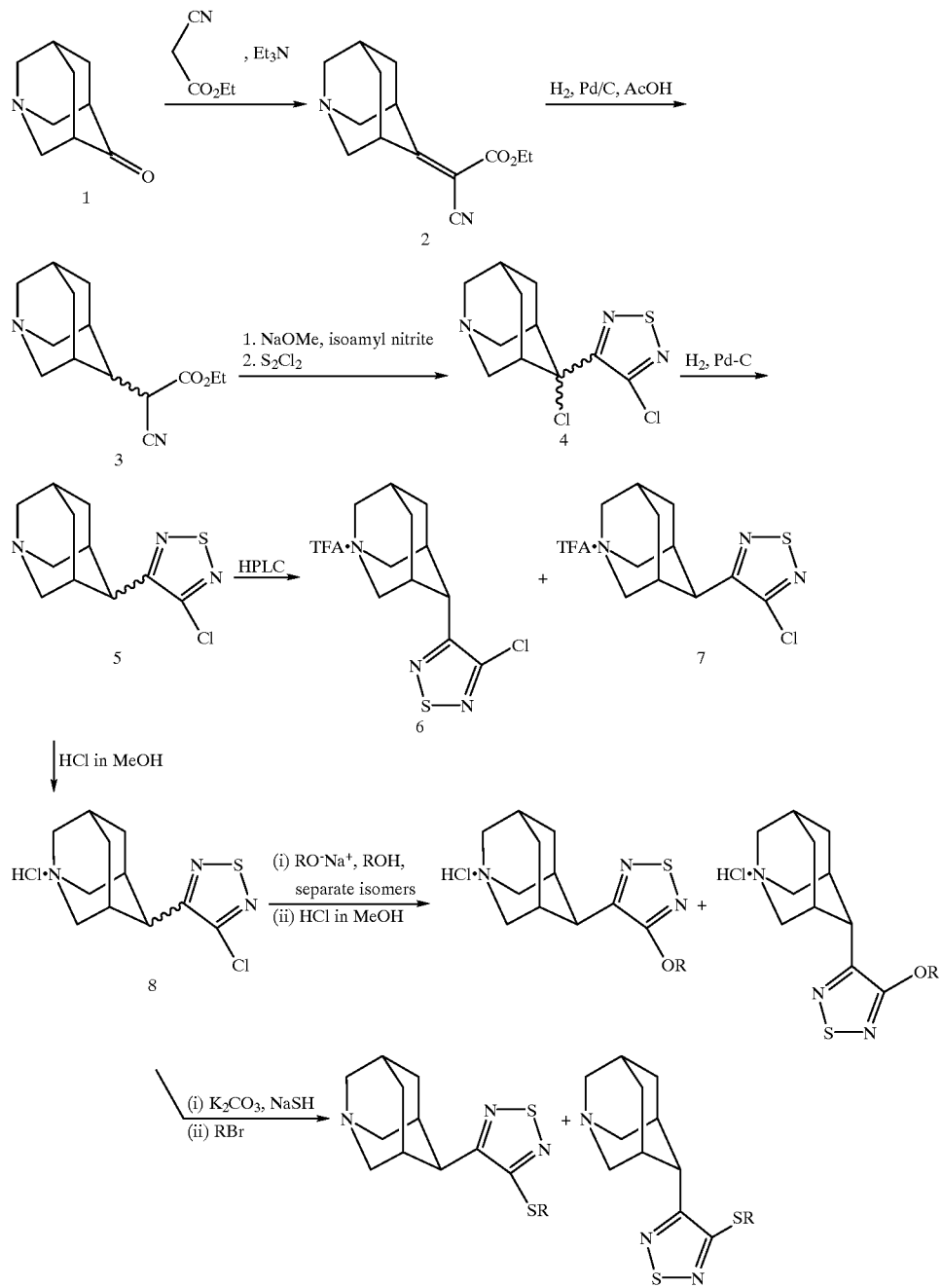
As described in the Examples, infra, the following compounds were made by the foregoing schemes:

TABLE 1
Azaadamantane Derivatives

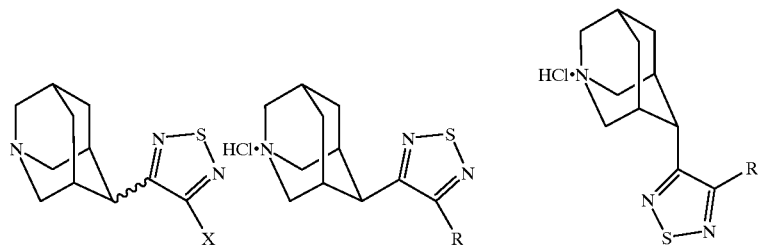

| Cmpd | X | Cmpd | R | Cmpd | R |
|---|---|---|---|---|---|
| 9 | —O-methyl | 20 | —O-methyl | 21 | —O-methyl |
| 10 | —O-ethyl | 22 | —O-ethyl | 23 | —O-ethyl |
| 19 | —O-propyl | 11 | —O-propyl | 12 | —O-propyl |
|  |  | 13 | —O-butyl | 14 | —O-butyl |
|  |  | 15 | —O-cyclopropylmethyl | 16 | —O-cyclopropylmethyl |
|  |  | 17 | —O-isobutyl | 18 | —O-isobutyl |
|  |  | 24 | —O-cyclopropylethyl | 25 | —O-cyclopropylethyl |
|  |  | 26 | —O-sec butyl | 27 | —O-sec butyl |
|  |  | 28 | S-propyl | 29 | —S-propyl |
|  |  |  |  | 30 | —S-ethyl |
|  |  |  |  | 31 | —S-butyl |
|  |  |  |  | 32 | —S-cyclopropylmethyl |

Synthesis of Oxadiazole Derivatives from 1-Azaadamantane-4-one

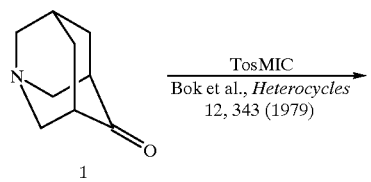

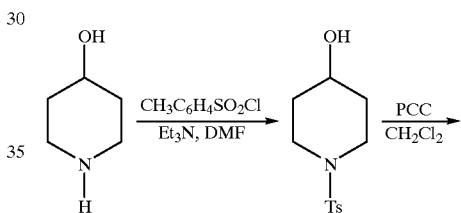

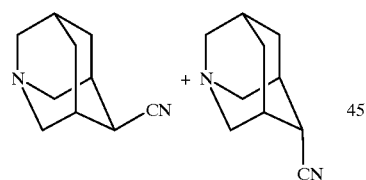

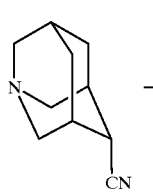

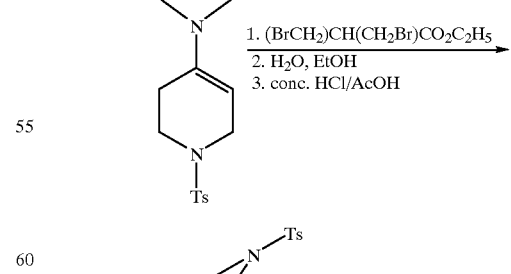

Synthesis of 3-Azanoradamantane-9-one

See, Bok et al., *Heterocycles* 12, 343 (1979); Speckamp et al., *Tetrhedron* 27, 3143 (1971); and Bok et al., *Tetrahedron* 35, 267 (1979); and Bok et al., *Tetrahedron* 33, 787 (1977).

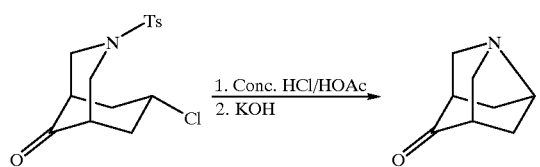
Synthesis of 3-Azanoradamantane-9-one Derivatives
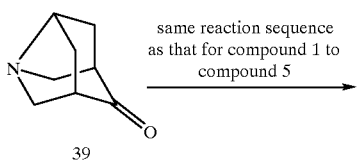
TABLE 2
Azanoradamantane Derivatives
| Cmpd | R | Cmpd | R |
|---|---|---|---|
| 33 | —O-ethyl | 34 | —O-ethyl |
| 35 | —O-propyl | 36 | —O-propyl |
| 37 | —O-isobutyl | 38 | —O-isobutyl |
| 41 | —S-propyl | 42 | —S-propyl |
Synthesis of 3-Azanoradamantane-6-one
See Bok et al., *Heterocycles* 12, 343 (1979).
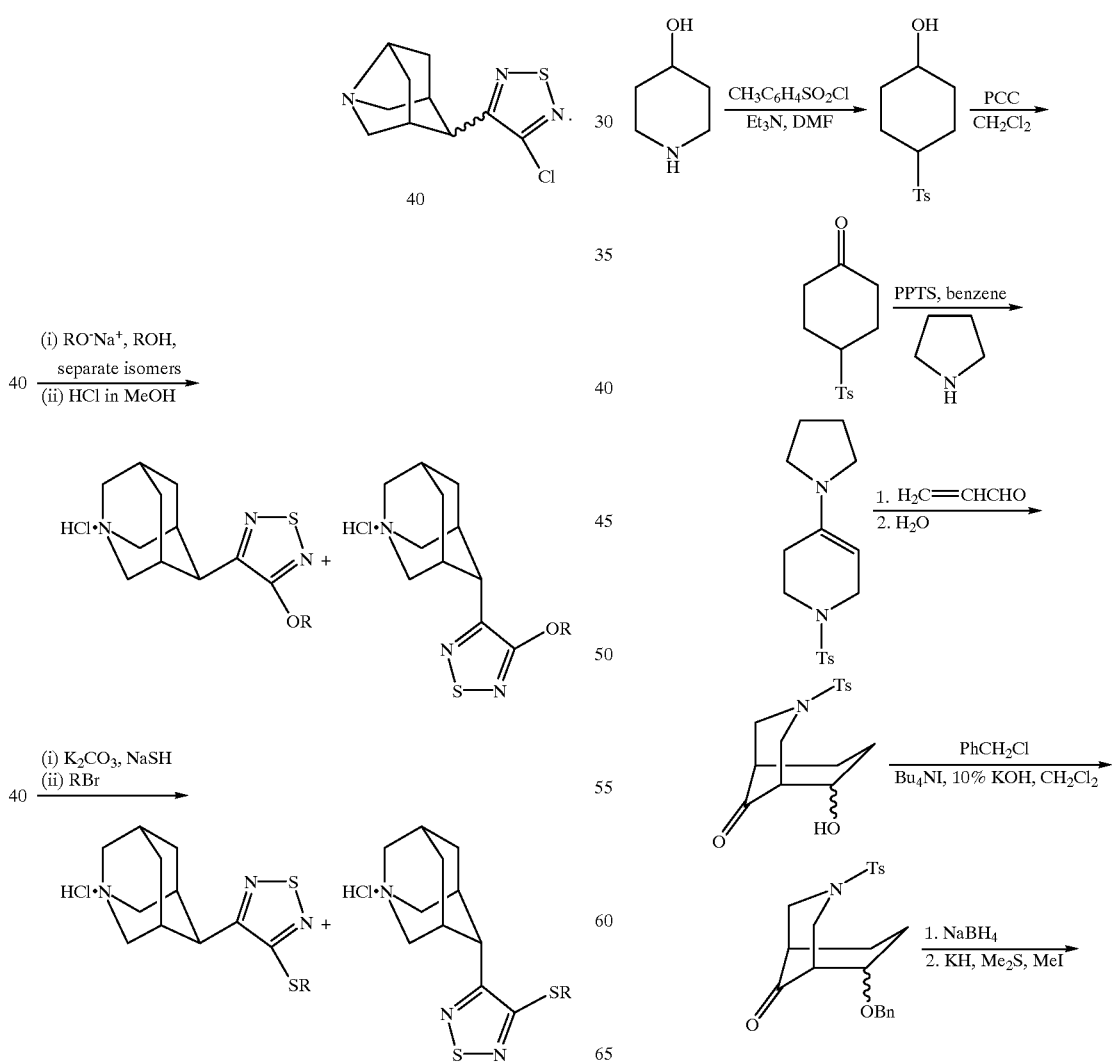

Synthesis of 3-Azanoradamantane-6-(chlorothiadiazole)

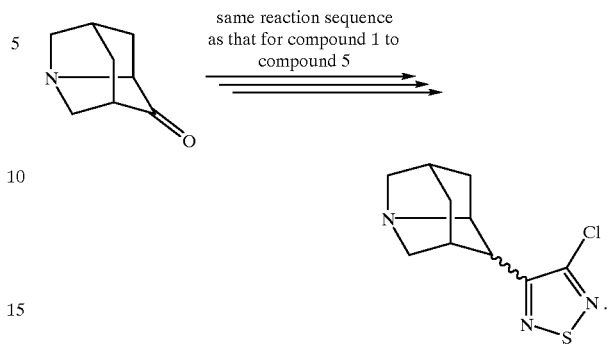

Synthesis of Azahomoadamantanes

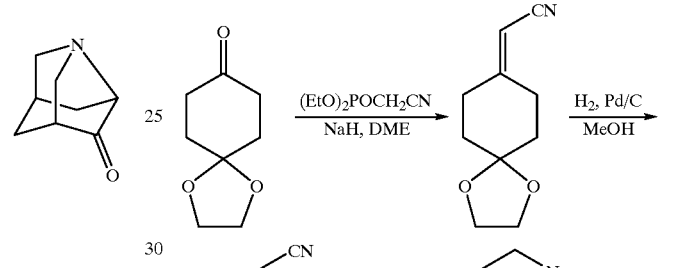

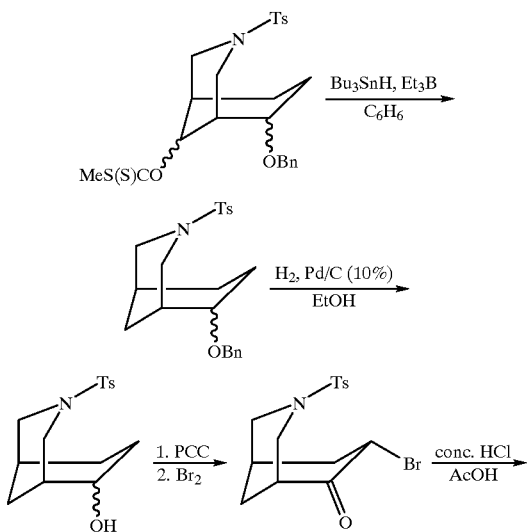

Alternatively, one may employ another similar approach:

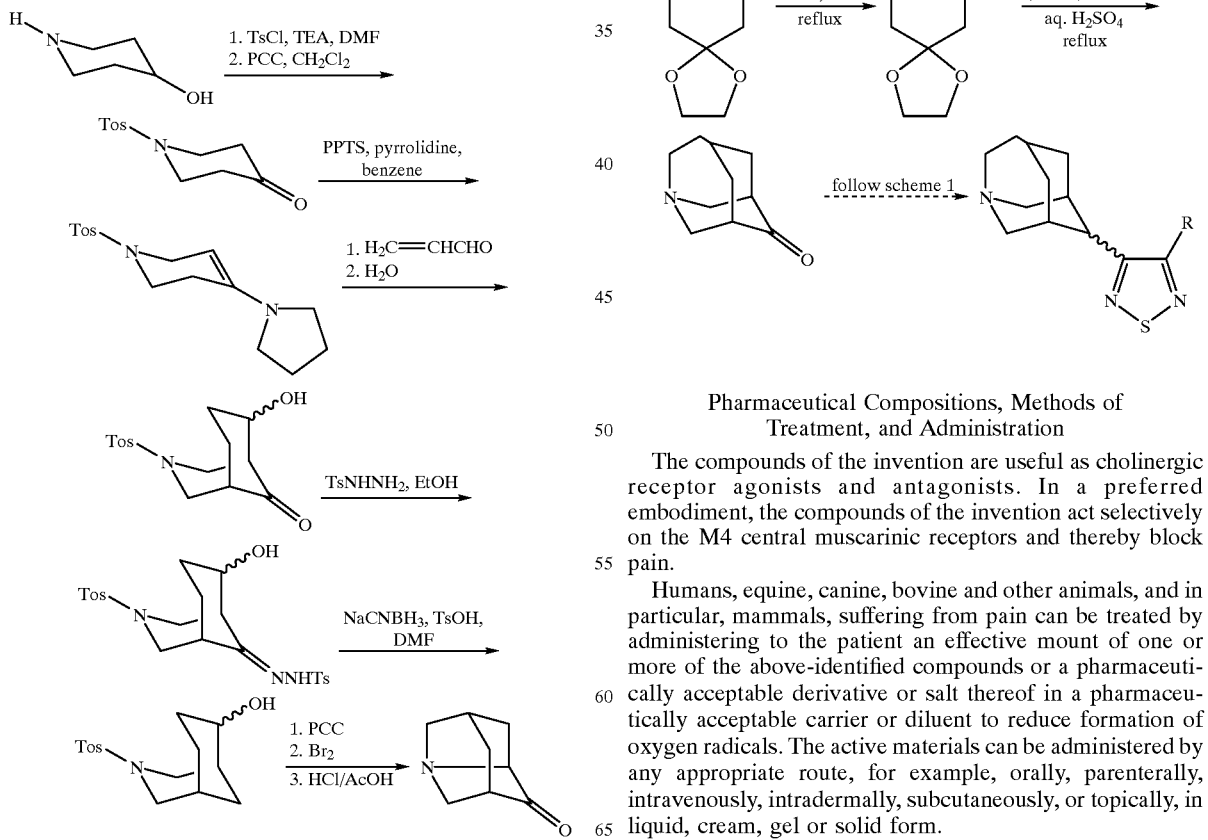

Pharmaceutical Compositions, Methods of Treatment, and Administration

The compounds of the invention are useful as cholinergic receptor agonists and antagonists. In a preferred embodiment, the compounds of the invention act selectively on the M4 central muscarinic receptors and thereby block pain.

Humans, equine, canine, bovine and other animals, and in particular, mammals, suffering from pain can be treated by administering to the patient an effective mount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is alkyl or benzyl, and Z is a counterion, including chloride, bromide, iodide, —O-alkyl, toluenesulfonate, methylsulfonate, sulfonate, phosphate, or arboxylate (such as benzoate, succinate, acetate, glycolate, maleate, malate, citrate, tartrate, ascorbate, benzoate, cinnalnoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The methods of the invention comprise administration to a mammal (preferably human) suffering from pain a pharmaceutical composition according to the invention in an amount sufficient to alleviate the pain. The compound is conveniently administered in any suitable unit dosage form, including but not limited to one containing 1 to 3000 mg, preferably 5 to 500 mg of active ingredient per unit dosage form. A oral dosage of 1–500, preferably 10–250, more preferably 25–250 mg is usually convenient.

The active ingredient should be administered to achieve peak plasma concentrations of the active compound of about 0.001–30 $\mu$M, preferably about 0.01–10 $\mu$M. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, other antiinflammatories, or antiviral compounds.

Solutions or suspensions used for parenteral, intradermal, subcutaneous, or topical application can include the following components: a sterile diluent such as water for injection, saline solution, fixed oils, polyethylene lycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Scios Nova (Baltimore, Md.). Liposomal suspensions may also be pharmaceutically acceptable carders. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

The following Examples are provided for illustrative purposes only and are not intended, nor should they be construed as limiting the invention in any manner. Those skilled in the art will appreciate that variations and modifications of the following Examples can be made without exceeding the spirit or scope of the invention.

EXAMPLES

Example 1

Ethyl 2-(5-azatricyclo[3.3.1.1<3,7>]dec-2-ylidene)-2-cyanoacetate (2)

A mixture of 5-(azatricyclo[3.3.1.1<3,7>]decane-2-one (Becker and Flynn, *Synthesis* 1992, 1080) (1, 5.0 g, 33 mmol), ethyl cyanoacetate (7.0 mL, 66 mmol) and triethylamine (6.9 mL, 49.5 mmol) was heated at 80° C. for 3 h. The mixture was cooled to room temperature and toluene (250 mL) was added to it. Toluene solution was washed with water (3×200 mL), dried over NaHCO$_3$ and rotavapped. The residue was dried on a hi-vac pump to give 2 (4.5 g, brown oil, 55%) which was used for the next step without further purification.

Example 2

Ethyl 2-(5-azatricyclo[3.3.1.1<3,7>]dec-2-yl)-2-cyanoacetate (3)

The crude product 2 (4.5 g, 18.3 mmol) was dissolved in absolute ethanol (100 mL). The solution was degassed by bubbling argon and to it was added glacial acetic acid (5 mL) and Pd/C (10%, 500 mg). The mixture was stirred under a hydrogen atmosphere overnight, filtered through a pad of celite, rotavapped and dried on hi-vac pump to give the acetate salt of the desired product. This residue was taken in methylene chloride (300 mL) and NaHCO$_3$ sat. solution (150 mL). Separated the organic layer and washed it with NaHCO$_3$ sat. solution (150 mLX3), dried over sodium sulfate and rotavapped to give 3 as a yellow oil (4.5 g, 99%).

Example 3

3-(5-Aza-2-chlorotricyclo[3.3.1.1<3,7>]dec-2-yl)-4-chloro-1,2,5-thiadiazole (4)

Sodium hydride (400 mg, 60% oil suspension, 10 mmol) was added to methanol/ethanol mixture (1:1, 15 mL). A solution of 3 (2.5 g, 10 mmol) in the same methanol/ethanol mixture (2 mL) was added and resulting reaction mixture was stirred at 1t for 30 min. It was cooled to 0° C. and isoamyl nitrite (1.5 mL, 11 mmol) was added to it. Stirred for 10 min. The solvent was removed on a rotavap and the residue was azeotroped with added toluene 3 times. The residue was dissolved in DMF (5 mL), cooled to 0° C. and was added to a cooled (0° C.) solution of S$_2$Cl$_2$ (2.4 mL, 30 mmol) in 2 mL of DMF dropwise with stirring. The mixture was stirred at rt for 48 h. The reaction was quenched by adding ice cold water (50 mL). The reaction mixture was heated at 70° C. for 30 min., filtered, cooled to rt and was basified with aqueous 4N NaOH solution. The resulting mixture extracted with toluene (3×100 mL). The combined extracts were washed with brine and dried over NaHCO$_3$. Solvent was removed on a rotavap and the residue was passed through a small column of silica gel, eluting with ammonia saturated methanol (5%) in chloroform, to obtain a mixture of the isomers 4 (800 mg, 28%), which contained minor impurities and was used without further purification.

Example 4

3-(5-Azatricyclo[3.3.1.1<3,7>]dec-2-yl)-4-chloro-1,2,5-thiadiazole (5)

The mixture of isomers 4 (800 mg, 2.76 mmol) was dissolved in 50 mL of ethanol and the resulting solution was degassed by bubbling argon. Pd/C (300 mg, 10%) was added and the reaction mixture was stirred under hydrogen atmosphere for 2 d. The mixture was filtered through celite and the catalyst was washed with methylene chloride containing 15% ammonia saturated methanol (200 mL). The filtrate was rotavapped the residue was subjected to radial chromatography using a chromatotron (eluent; 5% ammonia saturated methanol in methylene chloride) to give the mixture of isomers 5. A part of this mixture was separated into its two components 6 and 7 using HPLC (C$_{18}$, 7% acetonitrile in water+0.1% TFA). The pseudoasymmetry for these two components ('r' for 6 and 's' for 7) was assigned using NOE difference and homonuclear proton COSY experiments. The rest of the mixture 5 was dissolved in 2N aq. HCl in methanol (5 mL) and was concentrated under vacuum to give pale yellow solid 8 (300 mg, 37%).

Example 5

3-(5-Azatricyclo[3.3.1.1<3,7>]dec-2-yl)-4-alkoxy-1,2,5-thiadiazoles: General Procedure Sodium alkoxide was made by adding NaH (35 mg, 60% oil suspension, 0.9 mmol) into corresponding alcohol (5 mL) with stirring. The stirring was continued at rt for 30 min. The chlorothiadiazole 8 (25 mg, 0.08 mmol) was added to the resulting alkoxide solution and the reaction mixture was stirred at 60–70° C. over night. The solvent was removed under vacuum and the residue was taken in methylene chloride (20 mL), washed with water (2×20 ml) and brine (20 mL), dried over sodium carbonate and rotavapped. The residue was filtered through a small column of silica and then subjected to radial chromatography on a chromatotron, eluting with 5% ammonia saturated methanol in methylene chloride or reverse phase HPLC (YMC-pack ODS-AQ, 20X10 mm I.D., S-5 $\mu$M; mobile phase water:acetonitrile with 0.1% TFA) to obtain the 'r' and the 's' isomers, which were treated with methanolic HCl to give the corresponding hydrochloride salts.

Example 6

3-(5-azatricyclo[3.3.1.1<3,7>]dec-2yl)-4-methoxy-1,2,5-thiadiazoles (20 and 21)

The above mentioned general procedure was followed using methanol as the alcohol to give a crude mixture of 'r' and 's' isomers (10 mg, 50 %). A part of this mixture was used for separation of the isomers on HPLC (water:acetonitrile/80:20 with 0.1% TFA) followed by conversion to their HCl salts to give 0.5 mg of 20 and 1.3 mg of 21.

Example 7

3-(5-azatricyclo[3.3.1.1<3,7>]dec-2-yl)-4-ethoxy-1,2,5-thiadiazoles (22 and 23)

The above mentioned general procedure was followed using ethanol as the alcohol to give a crude mixture of 'r' and 's' isomers (10 mg, 50 %). A part of this mixture was used for separation of the isomers on HPLC (water:acetonitrile/75:25 with 0.1% TFA) followed by conversion to their HCl salts to give 1.5 mg of 22 and 0.8 mg of 23.

Example 8

3-(5-azatricyclo[3.3.1.1<3,7>]dec-2-yl)-4-propoxy-1,2,5-thiadiazole (11 and 12)

The above mentioned general procedure was followed using n-propanol as the alcohol to give 11 (12 mg) and 12 (6 mg, 71% combined for both 11 and 12).

Example 9

3-(5-azatricyclo[3.3.1.1<3,7>]dec-2-yl)-4-butoxy-1,2,5-thiadiazole (13 and 14)

The above mentioned general procedure was followed using n-butanol as the alcohol to give 13 (6 mg) and 14 (2.5 mg, 33% combined for both 13 and 14).

Example 10

3-(5-azatricyclo[3.3.1.1<3,7>]dec-2-yl)-4-(cyclopropylmethoxy)1,2,5-thiadiazole (15 and 16)

The above mentioned general procedure was followed using cyclopropylmethanol to give 15 (2 mg) and 16 (2 mg, 16% combined for both 15 and 16).

Example 11

3-(5-azatricyclo[3.3.1.1<3,7>]dec-2-yl)-4-(2-methylpropoxy)-1,2,5-thiadiazole (17 and 18)

The above mentioned general procedure was followed using iso-butanol as the alcohol to give 17 (4.6 mg) and 18 (2 mg, 26% combined for both 17 and 18).

Example 12

3-(5-azatricyclo[3.3.1.1<3,7>]dec-2-yl)-4-(cyclopropylethoxy)-1,2,5-thiadiazoles (24 and 25)

The above mentioned general procedure was followed using cyclopropylethanol as the alcohol to give 24 (2.2 mg) and 25 (2.7 mg, 20% combined for both 24 and 25).

Example 13

3-(5-azatricyclo[3.3.1.1<3,7>]dec-2-yl)-4-(1-methylpropoxy)-1,2,5-thiadiazoles (26 and 27)

The above mentioned general procedure was followed using sec-butanol as the alcohol to give 26 (1.3 mg) and 27 (2.4 mg, 15% combined for both 26 and 27).

Example 14

4-(5-Azatricyclo[3.3.1.1<3,7>]dec-2-yl)-4-alkylthio-1,2,5-thiadiazoles: General Procedure 3-(5-Azatricyclo[3.3.1.1<3,7>]dec-2-yl)-4-chloro-1,2,5-thiadiazole (8, 34 mg, 0.117 mmoles) was combined with anhydrous potassium carbonate (18 mg, 0.130 mmoles) and anhydrous sodium hydrogen sulfide (8 mg, 0.142 mmoles). To this dry, air-free mixture under argon was added anhydrous dimethylformamide (4 mL). This mixture was stirred at room temperature for 20 minutes at which time TLC showed no remaining chlorothiadiazole ($R_f$ 0.31, monitored on $SiO_2$ analytical plates using 10% $MeOH(NH_3)/CHCl_3$). At this time the mixture was cooled to 0° C. and to it was added corresponding 1-bromoalkane (0.40 mmoles). After stirring for 30 minutes at 0° C. the mixture was evaporated and purified using column chromatography (neutral alumina; 1% $MeOH(NH_3)/CHCl_3$) to yield the s and r isomers.

Example 15

4-(5-Azatricyclo[3.3.1.1<3,7>]dec-2-yl)-4-propylthio-1,2,5-thiadiazoles (28 and 29)

The above mentioned general procedure was followed using 1-bromopropane as the alkylbromide to give 28 (7.5 mg), 29 (4.2 mg, 33% combined for both 28 and 29) and 10 mg of the mixture of the two.

Example 16

4-(5-Azatricyclo[3.3.1.1<3,7>]dec-2-yl)-4-ethylthio-1,2,5-thiadiazole (30)

The above mentioned general procedure was followed using 39 mg of 8 and bromoethane as the alkylbromide to give 30 (4.8 mg 13%).

Example 17

4-(5-Azatricyclo[3.3.1.1<3,7>]dec-2-yl)-4-butylthio-1,2,5-thiadiazole (31)

The above mentioned general procedure was followed using 36 mg of 8 and 1-bromobutane as the alkylbromide to give 31 (2.6 mg 7%).

Example 18

4-(5-Azatricyclo[3.3.1.1<3,7>]dec-2-yl)-4-(cyclopropylmethyl)thio-1,2,5-thiadiazole (32)

The above mentioned general procedure was followed using 32 mg of 8 and cyclopropylmethylbromide as the alkylbromide to give 32 (5.1 mg 15%).

Example 19

4-(3-Azatricyclo[3.3.1.0<3,7>]non-9-yl)-3-chloro-1,2,5-thiadiazole (40)

40 was synthesized starting with 39 (see Bok et al., Heterocycles 12, 343 (1979); Speckamp et al., Tetrahedron 27, 3143 (1971); and Bok et al., Tetrahedron 35, 267 (1979); and Bok et al., Tetrahedron 33, 787 (1977)) following the synthetic scheme same as for the synthesis of 8 from 1.

Example 20

4-(3-Azatricyclo[3.3.1.0<3,7>]non-9-yl)-3-alkoxy-1,2,5-thiadiazoles: General Procedure Sodium alkoxide was made by adding NaH (15 mg, 60% oil suspension, 0.4 mmol) into corresponding alcohol (2 mL) with stirring. The stirring was continued at rt for 30 min. The chlorothiadiazole 40 (10 mg, 0.04 mmol) was added to the resulting alkoxide solution and the reaction mixture was stirred at 60–70° C. over night. The solvent was removed under vacuum and the residue was taken in methylene chloride (20 mL), washed with water (2×20 ml) and brine (20 mL), dried over sodium carbonate and rotavapped. The residue was filtered through a small column of silica and then subjected to reverse phase HPLC (YMC-pack ODS-AQ, 20X10 mm I.D., S-5 μM; mobile phase water:acetonitrile with 0.1% TFA) to obtain the 'r' and the 's' isomers, which were treated with methanolic HCl to give the corresponding hydrochloride salts.

Example 21

4-(3-Azatricyclo[3.3.1.0<3,7>]non-9-yl)-3-ethoxy-1,2,5-thiadiazoles (33 and 34)

The above mentioned general procedure was followed using ethanol as the alcohol to give 33 (1.1 mg) and 34 (0.9 mg, 19.2% combined yield).

Example 22

4-(3-Azatricyclo[3.3.1.0<3,7>]non-9-yl)-3-propyloxy-1,2,5-thiadiazoles (35 and 36)

The above mentioned general procedure was followed using propanol as the alcohol to give 35 (2.95 mg) and 36 (2.11 mg, 47% combined yield).

Example 23

4-(3-Azatricyclo[3.3.1.0<3,7>]non-9-yl)-3-isobutyloxy-1,2,5-thiadiazoles (37 and 38)

The above mentioned general procedure was followed using butanol as the alcohol to give 37 (2.51 mg) and 38 (1.68 mg, 47% combined yield).

Example 24

Tail-flick Assay

The tail flick assay is a commonly used animal model of analgesia. It is a stringent enough assay such that opiates (e.g., morphine) show activity in this model, whereas the non-steroidal antiinflammatories (NSAD's) such as ibuprofen are ineffective. As such, it is a useful assay system for investigating the utility of novel compounds for the treatment of severe and chronic pain.

Female CD-1 mice, weighing 20–30 grams were obtained from Charles River laboratories (Wilmington, Mass., USA). A commercially available tail-flick analgesia meter was used (Model TF-6 Analgesia Meter, Emdie Instrument Co., Maidens, Va.). The radiant heat source was set such that control mice had a tail-flick latency of 2–4 seconds. A 10-second cut-off time was used as the maximum latency to avoid damage to the mice tails. The latency of each mouse (a mean of two separate test results for each time-point), was obtained at 0 (immediately prior to dosing), 5, 15, 30, and 60 min. time-points after injection of compounds and the % Maximum Possible Effect (% MPE) was calculated by using the formula, % MPE=[(postdrug latency−predrug latency)÷(cutoff time−predrug latency)]×100. The results are presented in Table 1, infra.

Scoring of Salivation: The salivation was noted by close visual inspection of the animal's mouth and was scored according to the following scale: 0, no sign of saliva within animal's mouth; 1, evidence of saliva in animal's mouth, but none on animal's muzzle; and 2, evidence of saliva in animal's mouth and on animal's muzzle. Each animal was scored at 5, 15, 30 and 60 min time points after injection of compounds.

Body Temperature: At ambient temperature, a temperature probe (type T Thermocouple Thermometer, BAT-10; Physitemp Inc., Clifton, N.J.) was inserted 1.0 cm into the rectum of mice to measure their core temperature and recorded at 0 (before drug as a control baseline), 10, 25 and 55 min after injection of compounds.

Sedation: Sedation was noted by close visual inspection of the animal.

Example 25

Binding to Cloned Human M4 nA ChRs Expressed in CHO-K1 Cells

The following protocol was used to detect binding to cloned human M4 mAChRs expressed in CHO-K1 cells.

A membrane preparation was made from CHO-K1 cells expressing human M4 mAChRs. Aliquots of membrane were stored at −70° C. until thawed on the day of assay. For each assay, CHO-K1 M4 membrane preparation (approximately 20 μg of protein) was incubated with test compound and 2.5 nM $^3$H-oxotremorine M (DuPont, NEN) in 20 mM HEPES buffer, pH 7 in an assay volume of 200 μl. Assays were incubated in 96-well polypropylene plates for 40 minutes at room temperature. Nonspecific binding was determined in samples incubated in parallel in the presence of 10 μM atropine (Sigma) instead of test compound. The incubations were terminated by rapid vacuum filtration using a Packard plate harvester through 96-well Whatman GF/B filter plates presoaked in 0.5% polyethylenimine. The filter plate was washed rapidly four times with 0.2 ml aliquots of water. The plate was dried by placing under a heat lamp for 5 minutes. The plate was counted using a Packard scintillation counter after addition of 35 μl Microscint 20 scintillation fluid. Data were analyzed by nonlinear regression analysis.

Results from this assay are used to show the ability of compounds of this invention to bind to the agonist binding site of the muscalinic M4 receptor. Compounds which bind to this site have specific utility in the treatment of pain, schizophrenic disorders and cognitive disorders such as AD.

TABLE 3

| Cmpd | Salt | Tail-Flick $ED_{50}$ (mg/kg) | Side Effect Profile at $ED_{50\,Dose}$ | | | Human M4 in CHO-K1 Assay (nM) |
|---|---|---|---|---|---|---|
| | | | Salivation | Sedation | Hypothermia (° C.) | |
| 7 | TFA | — | — | — | — | >88 |
| 9 | HCl | >15 | — | — | — | 6.5 |
| 10 | HCl | 5.5 | — | — | — | 0.66 |
| 12 | HCl | 4.5 | 1.0 | Slight | 1.0 | 0.74 |
| 13 | TFA | — | — | — | — | 10 |
| 14 | HCl | >10 | 1.0 | Slight | 2.0 | 3.8 |
| 16 | HCl | 1.4 | 1.6 | Sedation | 1.5 | <1.4 |
| 18 | HCl | >5 | 0 | No sedation | 0 | — |
| 19 | — | 4 | — | — | — | 10 |
| 21 | HCl | >5 | 0 | No sedation | 0 | 5.9 |
| 23 | HCl | 1.5 | 0.4 | No sedation | 0.5 | 0.46 |
| 25 | HCl | 4.5 | 1.2 | Slight | 1.5 | — |
| 27 | HCl | >5 | 0 | No sedation | 0 | 1.55 |
| 29 | | <1 | 0 | Very slight | 0.5 | — |
| 30 | | 0.3 | 0.4 | Sedation | 1 | — |

TABLE 3-continued

| Cmpd | Salt | Tail-Flick ED$_{50}$ (mg/kg) | Side Effect Profile at ED$_{50}$ Dose | | | Human M4 in CHO-K1 Assay (nM) |
|---|---|---|---|---|---|---|
| | | | Salivation | Sedation | Hypothermia (° C.) | |
| 31 | | 0.3 | 0.6 | No sedation | 0 | — |
| 32 | | <1 | 1.2 | Sedation | <2 | — |
| 34 | HCl | >2 | — | — | — | 4.6 |
| 36 | HCl | >5 | — | — | — | 3.2 |
| 38 | HCl | >5 | — | — | — | — |
| 42 | | <2 | 2 | Sedation | 2 | — |

We claim:

1. An azacyclic ring system having the formula I

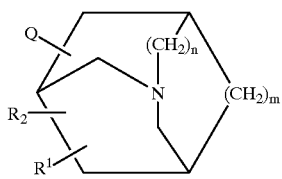

I including geometrical isomers, enantiomers, diastereomers, racemates, acid addition salts, and pharmaceutically acceptable salts thereof, wherein Q is

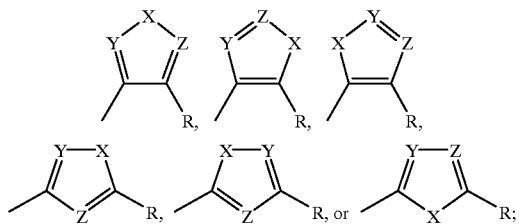

X is —CH$_2$—, —NH—, —O— or —S—;

V, W, Y and Z independently are CH or N;

n and m independently are 0, 1, 2, 3 or 4 provided n+m is greater or equal to 3;

R$^1$ and R$^2$ are at any position on the azacyclic ring, including the point of attachment of the heterocycle Q, and independently are hydrogen, —OH, halogen, —NH$_2$, carboxy, straight or branched C$_{1-10}$-alkyl, C$_{1-10}$-alkenyl, or C$_{1-10}$-alkynyl, straight or branched C$_{1-10}$-alkoxy, or straight or branched C$_{1-10}$-alkyl substituted with —OH, —CN, —CHO, —OH, —OR$^3$, —SR$^3$, —NH$_2$, —NHR$^3$, —NR$^3$R$^4$, —NO$_2$, —SOR$^3$, —SO$_2$R$^3$, —COR$^3$, —CO$_2$R$^3$, —CONH$_2$, —CONHR$^3$—CONR$^3$R$^4$, or —CH═NOR$^3$; or R$^1$ and R$^2$ independently are phenyl, phenoxy, benzoyl, benzyl or benzyloxycarbonyl, each of which are unsubstituted or substituted with halogen, —CN, C$_{1-10}$-alkyl, C$_{1-10}$-alkoxy, or C$_{1-10}$-alkylthio;

R is hydrogen, halogen, —CN, —CHO, —OH, —OR$^3$, —SR$^3$, —NH$_2$, —NHR$^3$, —NR$^3$R$^4$, —NO$_2$, —SOR$^3$, —SO$_2$R$^3$, —COR$^3$, —CO$_2$R$^3$, —CONH$_2$, —CONHR$^3$, —CONR$^3$R$^4$, or —CH═NOR$^3$; or R is phenyl, phenoxy, benzoyl, benzyl or benzyloxycarbonyl, each of which are unsubstituted or substituted with halogen, —CN, C$_{1-15}$-alkyl, C$_{1-10}$-alkoxy, or C$_{1-10}$-alkylthio; or R is a 5 or 6 membered saturated, partly saturated or aromatic heterocyclic ring containing one to three heteroatoms; and R$^3$ and R$^4$ independently are straight, branched, or cyclic C$_{1-15}$-alkyl, C$_{2-15}$-alkenyl, C$_{2-15}$-alkynyl, or combinations thereof, or R$^3$ and R$^4$ independently are phenyl, phenoxy, benzoyl, benzyl or benzyloxycarbonyl groups, each of which are unsubstituted or substituted with H, halogen, —CN, C$_{1-15}$-alkyl, C$_{1-10}$-alkoxy, C$_{1-10}$-alkylthio, or aryl; or R$^3$ and R$^4$ independently are 5 or 6 membered saturated, partly saturated or aromatic heterocyclic rings containing one to three heteroatoms.

2. The compound according to claim 1, wherein m+n is equal to 3.

3. The compound according to claim 1, wherein m+n is greater than 3.

4. The compound according to claim 1, wherein

X is S; and

Y and Z are N.

5. The compound according to claim 4, wherein m+n is equal to 3.

6. The compound according to claim 4, wherein m+n is greater than 3.

7. A pharmaceutical composition comprising a compound according to claim 1 and a pharmaceutically acceptable carrier.

8. A method of inducing analgesia, the method comprising administering an analgesia-inducing amount of a pharmaceutical composition according to claim 7 to a mammal in need thereof.

* * * * *

UNITED STATES PATENT AND TRADEMARK OFFICE
CERTIFICATE OF CORRECTION

PATENT NO.   : 6,323,194 B1                                                          Page 1 of 1
DATED        : November 27, 2001
INVENTOR(S)  : Grewal et al.

It is certified that error appears in the above-identified patent and that said Letters Patent is hereby corrected as shown below:

Column 19,
Line 63, please delete "4-(5-Azatricyclo[3.3.1.1<3,7>dec-2-yl)-4-alkylthio-" and insert therefor -- 3-(5-Azatricyclo[3.3.1.1<3,7>dec-2-yl)-4-alkylthio- --.

Column 20,
Line 16, please delete "4-(5-Azatricyclo[3.3.1.1<3,7>dec-2-yl)-4-" and insert therefor -- 3-(5-Azatricyclo[3.3.1.1<3,7>dec-2-yl)-4- --.
Line 25, please delete "4-(5-Azatricyclo[3.3.1.1<3,7>dec-2-yl)-4-ethylthio-" and insert therefor -- 3-(5-Azatricyclo[3.3.1.1<3,7>dec-2-yl)-4-ethylthio- --.
Line 33, please delete "4-(5-Azatricyclo[3.3.1.1<3,7>dec-2-yl)-4-butylthio-" and insert therefor -- 3-(5-Azatricyclo[3.3.1.1<3,7>dec-2-yl)-4-butylthio- --.
Line 42, please delete "4-(5-Azatricyclo[3.3.1.1<3,7>dec-2-yl)-4-" and insert therefor -- 3-(5-Azatricyclo[3.3.1.1<3,7>dec-2-yl)-4- --.

Signed and Sealed this

Twenty-sixth Day of November, 2002

*Attest:*

*Attesting Officer*

JAMES E. ROGAN
*Director of the United States Patent and Trademark Office*